United States Patent
Nyirucz et al.

(10) Patent No.: US 10,814,076 B2
(45) Date of Patent: Oct. 27, 2020

(54) METHOD FOR ENHANCING EUSTACHIAN TUBE PATENCY AND TREATMENT OF OTITIS MEDIA

(71) Applicants: Alex Nyirucz, Bellerose, NY (US); Richard Lee Strauss, Freeport, NY (US); Alan Joseph Mautone, Morristown, NY (US)

(72) Inventors: Alex Nyirucz, Bellerose, NY (US); Richard Lee Strauss, Freeport, NY (US); Alan Joseph Mautone, Morristown, NY (US)

( * ) Notice: Subject to any disclaimer, the term of this patent is extended or adjusted under 35 U.S.C. 154(b) by 122 days.

(21) Appl. No.: 16/350,850

(22) Filed: Jan. 23, 2019

(65) Prior Publication Data
US 2019/0160233 A1    May 30, 2019

Related U.S. Application Data

(63) Continuation-in-part of application No. 15/530,366, filed on Jan. 3, 2017, now Pat. No. 10,195,376.

(51) Int. Cl.
| | |
|---|---|
| *A61M 11/02* | (2006.01) |
| *A61M 15/08* | (2006.01) |
| *A61M 15/00* | (2006.01) |
| *A61F 11/00* | (2006.01) |
| *A61M 31/00* | (2006.01) |

(52) U.S. Cl.
CPC ............ *A61M 11/02* (2013.01); *A61F 11/00* (2013.01); *A61M 15/009* (2013.01); *A61M 15/08* (2013.01); *A61M 15/085* (2014.02); *A61M 31/00* (2013.01); *A61M 2202/0488* (2013.01); *A61M 2205/583* (2013.01); *A61M 2210/0618* (2013.01); *A61M 2210/0675* (2013.01)

(58) Field of Classification Search
CPC .... A61K 9/008; A61K 9/0043; A61K 9/0075; A61K 9/0078; A61K 45/06; A61K 9/0073; A61K 9/006; A61K 9/0014; A61M 15/08; A61M 15/009; A61M 11/00
See application file for complete search history.

(56) References Cited

U.S. PATENT DOCUMENTS

2011/0152838 A1 * 6/2011 Xia ........................ A61M 15/08
604/514

* cited by examiner

*Primary Examiner* — Manuel A Mendez
(74) *Attorney, Agent, or Firm* — Richard L. Strauss, esq.

(57) ABSTRACT

A method of increasing eustachian tube patency in human patients is disclosed wherein a eustachian tube targeting nasal administration device is utilized to deliver a surfactant/propellant mixture to the nasopharyngeal stoma of the auditory tube. The targeting capability of the administration device obviates the need for a spreading agent that would otherwise be required to enable at least a portion of surfactant to reach the eustachian tube orifice. More specifically, the non-targeting, indiscriminate delivery provided by nasal administration devices of the past required surfactant to spread over non-targeted tissue it was inadvertently applied to in order to reach the eustachian tube stoma. In addition, a method for treatment of otitis media is disclosed utilizing, in some preferred embodiments, a therapeutically active agent.

29 Claims, 8 Drawing Sheets

METHOD FOR ENHANCING EUSTACHIAN TUBE PATENCY AND TREATMENT OF OTITIS MEDIA

RELATED APPLICATIONS

This is a continuation-in-part application of U.S. patent application Ser. No. 15/530,366, filed Jan. 3, 2017, the complete specification and drawings of which are hereby incorporated by reference.

TECHNICAL FIELD

This application relates to the field of nasally administered mixtures, medications, compounds and compositions (hereinafter collectively referred to as "compositions") especially formulated for the treatment of the eustachian tube dysfunction and otitis media. This application also relates to nasal administration devices especially designed, configured and adapted to deliver such compositions to the eustachian tube by targeting the pharyngeal orifice of that structure with a collimated stream of such compounds.

BACKGROUND OF THE ART

U.S. patent application Ser. No. 15/530,366 (the "'366 application") discloses multiple embodiments of administration devices which enable targeted delivery of compositions through the nasal orifice of a patient to the nasopharyngeal orifice of the eustachian tube. The devices disclosed comprise an administration housing in which a canister of a compound to be delivered is contained. The administration housing includes a canister containment section and a delivery nozzle section. The delivery section includes a collimating delivery nozzle. In certain embodiments of the eustachian tube targeting administration devices disclosed in the '366 application, a canister containment section alignment tab extends from the canister containment section. This administration device, as well as all embodiments disclosed in the '366 application, provides a means of delivering a collimated stream of compositions in such a manner that the longitudinal axis of the collimated stream of compound emanating from the delivery nozzle is directed towards the eustachian tube stoma. The term "targeted delivery" and "eustachian tube targeting nasal administration device" all refer to those devices, disclosed within the '366 application, which direct a collimated stream of compound(s) to the nasopharyngeal orifice of the eustachian tube by means of their design, configuration and positioning indicators.

More specifically, in a first preferred embodiment of the device claimed and disclosed within the '366 application, a delivery nozzle of the device, located upon a front surface of the delivery nozzle section, is placed within a patient's nostril while, at the same time, a containment section alignment tab, extending from the housing of such device, is positioned and stabilized against the bridge portion of the patient's nose. Once placed in this position, the design, shape, configuration and dimensions of this device orients the delivery nozzle so that a collimated stream of compounds that is released from the nozzle to device activation, targets the nasopharyngeal orifice of the eustachian tube located on the same side of the patient's face as is the nostril entered. The delivery nozzle demonstrates a central bore and proximal and distal orifices communicating therewith which are of equal and continuous diameter. The diameter selected for these structures enables the collimation of the compounds emanating therefrom.

Such embodiments may further comprise an elevation alignment line/arrow formed within or upon the side walls of a delivery nozzle section of the housing which is formed and configured to be in parallel alignment with the longitudinal axis of the central bore of the delivery nozzle. In targeting the eustachian tube with such devices, the housing is further positioned so that the elevation alignment line/arrow in alignment with an imaginary reference line (the "nostril/tragus reference line") running from the patient's nostril to the tragus of the ear on the same side of the patient as the nozzle entered. Such positioning further assures that the collimated stream of compound emanating during device activation is in alignment with and thus targets the eustachian tube stoma. Certain preferred embodiments further comprising a delivery section alignment tab, which is designed for placement and further stabilization of the device in the region of the patient's philtrum, one or both of the cannister alignment and delivery section tabs may be adjustable so as to align the elevation line/arrow as discussed above. Such adjustment of the alignment tabs and concomitant adjustment of the device's position, further assures that the collimated stream emanating from the device to be directed towards the pharyngeal opening of the eustachian tube.

In a second alternate embodiments of the '366 application, a nasal administration device is disclosed and claimed comprising a collimation nozzle and an administration housing. As with all other embodiments of the administration device disclosed in the '366 application, the second alternate embodiment is especially designed, configured and adapted for the accurate targeted delivery of a collimated stream of compositions to the pharyngeal orifice of the eustachian tube.

The administration housing of the second alternate embodiment is comprised of a canister containment section and a delivery nozzle section. The canister containment section advantageously includes two finger rests extending from the outer surface of the front and rear portions of the canister containment section adjacent the proximal terminus thereof located approximately opposite one another (in a 180 degree relation). The finger rests provide, as discussed below, a means of holding and easily manipulating the position of the device during use as well as finger holds to press against when depressing the canister bottle (which extends from the superior terminus of the housing). The back portion of canister containment section includes a midline alignment line so as to aid in positioning the device (as described in more detail, below).

The second alternate embodiment of the administration device disclosed in the '366 application includes a collimating delivery nozzle which is positioned upon and arises from the delivery nozzle section. More specifically, it arises from the front surface of this section and approximately 180 degrees opposite the midline alignment mark located upon the back surface of the cannister containment section. This configuration enables an individual, administering compounds to a patient with the device, to view the midline alignment mark and manipulate the position of the housing so that it is aligned with the midline of the patient's face after inserting the delivery nozzle into the patient's nostril. The second alternate embodiment, although highly efficient in administering compound(s) to the eustachian tube of infants and noncompliant patients, is effective for such delivery to all patients, regardless of age or compliance level.

The term "composition" and "compound(s), as utilized throughout the '366 application and claims, refers to any composition(s), mixture(s) and/or medicaments which can be utilized for the treatment of any condition and/or, pathology involving the eustachian tube, middle ear, or the enhancement of any function of the eustachian tube or middle ear which utilizes application of such materials to or through the eustachian tube of a patient.

All of the administration devices disclosed in the '366 application—which are utilized in practicing the methods of the present invention as discussed, below—may be advantageously utilized, for example, in conjunction with a metered dose canister bottle contained within the administration housing. This canister, in certain preferred embodiments, is the source of compositions to be delivered by the '366 device. The disclosure set forth within that application also contemplates using the claimed device for the administration of compositions contained in other metered and non-metered dose canisters so long as such canisters are capable of providing, upon actuation, a stream of such compounds(s), compositions and/or medications capable of flowing through aid being delivered by the device, as described above and below. The canisters utilized may also be integrated as a continuous part of the administration housing—without the need for a separate canister element—. The '366 application also contemplated that the disclosed device may be utilized with medication contained within "blister packs", the contents of which are propelled through the device by a liquid propellant, compressed gas, or pump actuation utilizing atmospheric air One of the most significant and useful utilities of embodiments of the '366 administration device is the ability thereof to direct a collimated (focused) stream of a selected composition, mixture or compound directly towards the pharyngeal opening of the eustachian tube. Prior to the '366 disclosure, nasal administration devices had been devoid of any means of selectively directing compositions towards this target (eustachian tube stoma) or, for that matter, any particular target.

U.S. Pat. No. 6,156,294 ('the '294 patent') discloses compositions effective in treating otitis media, decreasing eustachian tube opening pressure and delivering compositions effective in treating otitis media. More specifically, the '294 patent discloses a process, composition and method for increasing and enhancing mammalian eustachian tube lumen patency and pressure equalization performance. This patent teaches the production and use of an aerosolized mixture of lipid crystals comprised of a mixture of one or more lipids surfactants and one or more spreading agents— all in dry powdered form—selected from the group consisting of sterols, lipids, fatty acids, cholesteryl esters, phospholipids, carbohydrates, and proteins, in powder form, and one or more propellants, in which the lipid surfactants and spreading agents are not soluble. The method of the '294 patent discloses administration of a mixture of these components, through a mammalian nasal orifice. Upon administration, the propellant(s) are evaporated from the mixture and the lipid crystals are deposited upon the mucosa lining a patient's nasal cavity, nasopharynx and adjacent sinuses.

Eventually, through the action and effect of the required spreading agent constituent, a portion of the disclosed compositions come into contact with lumen surfaces of the eustachian tube forming an amorphous spread film thereupon. The surfactant component acts upon the air/liquid interface resident upon the mucosa lining the lumen so as to substantially decrease the opening pressure. Such reduction in opening pressure enables the auditory tube lumen to open to a greater extent and more frequently. Opening of the lumen, in turn, enables improved and more frequent pressure equalization as well as improved draining functions (of the middle ear chamber).

The '294 patent also discloses, in a second preferred embodiment, a method, process and composition wherein a therapeutically active agent(s) effective in the treatment of otitis media—also in dry powdered form and insoluble within the propellant—is added to the mixture of lipid crystals (formed from lipid surfactant and spreading agent). Upon administration of said aerosol mixture, the amorphous spread film formed thereby, enabled in great part by the spreading agent constituent, carries the therapeutically active agent along the surfaces of the nasal cavity, to and through the pharyngeal orifice of the eustachian tube and ultimately, through the lumen of the auditory tube to the tissues of the middle ear. Within the middle ear chamber, as well as within the lumen of the auditory tube, the therapeutically active agent acts to resolve causative infections, inflammation and/or congestion while the surfactant component lowers eustachian tube opening pressure to enable enhanced draining of the middle ear chamber.

In all embodiments disclosed in the '294 patent, there are, in regard to the disclosed composition, at minimum, 3 required elements. First, there is at least one lipid surfactant whose function is to decrease the surface tension of the air/liquid interface resident upon the epithelial lining of the eustachian tube. Secondly, there is at least one spreading agent required to enable and accelerate the surfactant's spread across the nasal cavity mucosa so that a portion of the surfactant reaches the eustachian tube opening (stoma) within the nasopharynx. Thirdly, the methods, compositions and processes disclosed in the '294 patent require a propellant constituent in which neither the spreading agent or the surfactant is soluble.

In order to allow DPPC to spread more rapidly, the rigidity and packing of the DPPC membrane must be perturbed (disrupted) by what is termed a spreading agent. For this reason, the prior art teachings of the '294 patents as well as other related patents such as U.S. Pat. Nos. 6,616,913 and 6,676,930, all teach the requirement that dry powdered lipid surfactants, such as DPPC, delivered by a propellant in which no constituents are soluble, must be combined with a spreading agent.

The flow (or spread) of the mixture of surfactant enabled by the spreading agent is required due to the fact that prior art nasal administrators instilled compositions, such as the aforementioned surfactant/spreading agent composition, in a rather haphazard, shotgun-like manner depositing the composition randomly about the nasal cavity, nasopharynx and adjoining sinus cavities. Even devices capable of providing a narrow stream upon actuation, were devoid of any mechanism or guidance to direct such streams towards the eustachian tube stoma.

The specific and most preferred example of surfactant identified within the '294 patent is the phospholipid 1,2 dipalmitoyl, phosphatidlycholine (DPPC). DPPC is the most surface active of the phospholipids or any of the subclass of fully saturated acyl chain phospholipids. That is to say that DPPC, in combination with any spreading agent(s) disclosed therein, has a maximum effect in reducing surface tension at an air/liquid interface. Likewise, the '294 patent identifies preferred spreading agents as cholesteryl palmitate (CP) and diacylphosphatidylglycerol (PG).

The '294 patents disclosed requirement requiring both a surfactant and spreading agent presents several difficulties. Firstly, in order to provide a pharmaceutically acceptable medication, the ratios of surfactant and spreading agent must remain constant during the manufacturing process, storage, and for a substantial time period thereafter. In addition, each activation of, for example, a metered dose nasal administration device, must by shown to deliver the same ratio of one component compared to the other (e.g., surfactant/spreading agent ratios). Mixtures of two or more constituents within a propellant inherently cause greater difficulty in meeting regulatory requirements such as achieving consistent formula ratios, stability of multi-constituent formulations of time and avoidance of agglomeration. Furthermore, utilizing both a surfactant and a spreading agent is costlier than utilizing a single component formula wherein only a surfactant is present. In addition, since only a relatively small portion of surfactant reaches the target eustachian tube opening, more of the composition is needed so that an effective amount of surfactant reaches the target eustachian tube lumen.

Acute otitis media, especially in a child, in very often accompanied by severe pain due, in great part, to pressurization of the middle ear and the eustachian tube's inability to open so as to relieve such pressure. Especially in regard to pediatric care, rapid relief of acute pain is of paramount importance It would be highly advantageous if a method were disclosed enabling targeted delivery of a surfactant effective, in lowering eustachian tube opening pressure—directly towards the eustachian tube orifice—. Such a method would be an inherently faster way of bringing pain relief to such a child by enabling restoration of the pressure equalization and drainage functions of the eustachian tube. The time delay required to enable surfactant, spayed throughout the nasal cavity and adjacent passageways and structures, to reach the eustachian tube stoma could be eliminated with a targeted delivery. For the same reasons, disclosure of a method providing targeted delivery of a surfactant to the auditory tube lumen, effective in reducing opening pressure of the eustachian tube lumen, while, simultaneously, delivering therapeutic agents effective in the treatment and resolution of otitis media to the middle ear chamber—without need of a spreading agent—would be equally beneficial.

SUMMARY OF THE INVENTION

Now, in accordance with first preferred method of the present invention, a method is disclosed for enhancing eustachian tube functions. Such functions include enablement and improvement of pressure equalization—between the middle ear chamber and ambient atmosphere pressure—normally provided by a patent eustachian tube lumen. In addition, such enhanced functions also refer to enablement and improvement of the drainage functions of the eustachian tube in emptying byproducts excreted and formed within the middle ear chamber during, for example, episodes of otitis media. Such byproducts include inflammatory exudates and other secretions which collect within the middle ear as the result of viral, bacterial and immune responses thereto.

In practicing the method of the first preferred embodiment, a collimated stream of a surfactant/propellant mixture is delivered to the eustachian tube lumen of a human patient utilizing an eustachian tube targeting nasal administration device. The term "eustachian tube targeting nasal administration device" refers to those devices disclosed and claimed within the '336 application which direct a collimated stream of compounds to the nasopharyngeal orifice of the eustachian tube of a human patient. In practicing the method of the first embodiment, the targeting nasal administration device may be advantageously comprised of an administration housing having an alignment tab depending therefrom especially shaped and configured for stable placement upon the bridge portion of a patient's nose. The administration housing contains a mixture consisting of two constituents—a surfactant and a propellant—, as described below. The device further comprises a delivery nozzle section especially designed and configured to be inserted within and provide stable contact with a nostril on a selected side of the patient's nose. The delivery nozzle is formed and configured to demonstrate a proximal and distal opening and a central bore of a constant and continuous diameter, the diameter being especially selected to optimize collimation of the selected mixture of surfactant and propellant contained within the administration housing. Due to the size, shape and configuration of the device, when so positioned upon the bridge portion of the patient's face and within the patient's nostril, upon activation thereof, the device releases and directs a collimated stream of the mixture of surfactant and propellant towards the nasopharyngeal orifice of the eustachian tube on the same side of the patient's face as the nostril into which the nozzle was inserted. Due to the targeted delivery of the selected mixture of surfactant and propellant, a spreading agent is not required in order to efficiently and effectively cause the mixture to reach and enter the lumen of the patient's eustachian tube. Once the mixture reaches the lumen, it effectively reduces the surface tension of the air/liquid interface resident thereupon. This reduction in surface tension, in turn, substantially reduces the opening pressure of the eustachian tube so that the normal physiologic functions of middle ear pressure equalization and middle ear fluid drainage are restored and/or enhanced. Thus, the "patency" or open condition of the lumen of the auditory tube is enhanced so that it is more easily and effectively achieved. The term "effectively reduces opening pressure of the eustachian tube" refers to the effect of the surfactant in reducing the surface tension of the air/liquid interface resident upon the eustachian tube lumen's lining epithelium. This reduction of surface tension, in turn, reduces the force necessary to open the eustachian tube lumen so that normal anatomical and physiological activities, such as swallowing, rotation of the head provide sufficient force so as to open the eustachian tube. Such lumenal opening enables enhanced pressure equalization function (of pressure differentials between the middle ear chamber and ambient atmospheric pressure) and also allows enhanced drainage of contents of the middle ear chamber into the nasopharynx. Thus, the first embodiment of the present invention also provides a method of treating otitis media in enabling inflammatory and infectious byproducts of OM to drain from the middle ear chamber so as to speed resolution of that pathological condition.

Eustachian tube targeting nasal administration devices especially useful in practicing the first preferred method may advantageously include an elevation alignment line/arrow positioned upon the side surfaces of the delivery nozzle section. The elevation alignment line/arrow is placed and positioned so as to be in parallel alignment with the central bore of the delivery nozzle mounted upon the delivery nozzle section. Such devices may also include an alignment tab depending from the canister containment housing which is especially shaped, configured and positioned to be placed in stable contact with the bridge portion of a patient's nose while the delivery nozzle is placed within the patient's nostril on one side of the patient's face. Thereafter, the device is further manipulated and positioned so that the elevation alignment line is aligned with and points to the tragus of the ear on the same side of the patient's face as the nostril entered by the delivery nozzle. The device is thereafter activated releasing a collimated stream of the surfactant/propellant mixture directly towards the eustachian tube orifice. The delivery nozzle of all embodiments of the eustachian tube targeting nasal administration device demonstrates a smooth central bore continuous with a proximal and distal opening. The central bore, proximal and distal openings of the nozzle all demonstrate the same continuous diameter. In addition, the diameter is selected in accordance with the characteristics of the mixture so as to yield a desired collimated stream. Since the elevation alignment mark/arrow is in alignment with the central bore of the administration nozzle, and the elevation alignment line/arrow is directed towards the tragus, the collimated spray released from the device during activation is directed along the nostril/tragus reference line and so is also aligned with the nasopharyngeal eustachian tube opening.

As stated above, the eustachian tube targeting nasal administration devices disclosed and claimed within the '366 application are the devices utilized in practicing the method of the first preferred embodiment. Some embodiments of these devices include a midline alignment line positioned in the middle of the back surface of the canister containment section. These midline alignment lines are so positioned and formed so as to be aligned with the longitudinal axis of the central bore of the administration housing. When utilizing such devices in practicing the first preferred method of the present invention, the alignment tab depending from the front surface of the canister containment housing is placed in firm and stable contact with the bridge portion of a patient's nose while the delivery nozzle is placed within the patient's nostril on one side of a patient's face. Thereafter, the device is further manipulated and positioned so that the elevation alignment line/arrow, formed on the side surfaces of the delivery nozzle section points towards the tragus of the ear on the same side of the patient's face as nostril entered. The device is further positioned to ensure that the midline alignment line is aligned with the midline of the patient's face. Such further alignment assures that the collimated spray directed along an elevation leading to the eustachian tube stoma does not deviate medially or laterally. Some embodiments of these targeting administration devices may include a midline alignment line, but not include an elevation alignment line/arrow. In such instances, positioning the canister alignment tab against the bridge portion of the patient's nose with the administration nozzle within the nostril on a selected side of the patient's face cause the longitudinal axis of the collimated stream to be in elevational alignment with the eustachian tube stoma. Further positioning the device so that the midline alignment line is aligned with the midline of the patient's face, further improves accuracy in guiding the collimated stream towards the eustachian tube's nasopharyngeal stoma by avoiding medial or lateral deviation of the stream. To further assure and stabilize the above described positioning and to fine tune targeting of the collimated stream, certain embodiments of the eustachian tube targeting nasal administration devices utilized in practicing the first preferred method utilize adjustable alignment tabs which are positioned upon the bridge portion of the nose which can be adjusted until, for example, stable position of the tab on the bridge portion of the patient's nose occurs when, for example, the elevation alignment line/arrow points towards the tragus of the patient's ear on the same side of the patient's face as the nostril entered by the nozzle. Other preferred eustachian tube targeting nasal administration devices include an additional alignment tab, depending from the delivery nozzle section, which are placed in stable contact with the philtral columns above the patient's lip. Such additional alignment tabs may also be adjustable so as to enable consistent targeting of the eustachian tube verified via the above-discussed elevation alignment line/arrow and midline alignment line.

In all embodiments of the first preferred method of the present invention, no other constituent beyond a surfactant constituent and propellant constituent is administered by the targeting administration device. The targeting aspect of all methods of the present invention eliminate the need to include a spreading agent.

In practicing all methods of the present invention, the surfactant is selected from cholesteryl esters, phospholipids, carbohydrates, and proteins, all, preferably, in powder form. However, it is preferred that said surfactant be selected to be a phospholipid, and still further preferred that said phospholipid be selected to be of the class phosphatidlycholine including any fully saturated diacyl phosphatidylcholine including 1,2 dipalmitoyl phosphatidylcholine (DPPC). It is preferred that the surfactant be in a dry powdered form demonstrating a particle size of from about 1 to about 50 microns. It is still further preferred that the surfactant demonstrate a particle size of from about 10 to about 40 microns. It is still further preferred that the powdered surfactant demonstrate a particle size of from about 1 to about 15 microns.

It is preferred that the surfactant constituent of the mixture of surfactant and propellant be insoluble within the propellant at manufacturing, storage and delivery temperatures. Thus, the surfactant, when utilized with a liquid propellant, will ordinarily form a colloidal suspension but retain the particle size ranges disclosed above. Such diminutive particle size ranges enhance the collimation of the administered stream emanating from the administration and speeds the entry of the crystals into an amorphous state upon contact with the air/liquid interface resident upon the mucosa about the eustachian tube stoma and lining the lumen thereof. Such diminutive particle size also reduces device the incidence of agglomeration of the surfactant particles and clogging of the nozzle resulting therefrom.

In practicing all embodiments of the present invention, the propellant may be advantageously selected to be fluorocarbon propellant such as, for example, chlorofluorocarbon propellants, hydrofluorocarbons or mixtures thereof. Carbon dioxide, as well as pressurized air may also be utilized as the propellant. In fact, the propellant may be any pharmaceutical grade, hypo-allergenic propellant in which the surfactant is not soluble. In those embodiments of the present invention wherein a therapeutically active agent is utilized, such active agent must also be in a powdered form and also be insoluble within the propellant at the usual ranges of manufacturing, storage and physiologic application temperatures. More specifically, neither the surfactant nor, in the case of embodiments incorporating a therapeutically active agent, can that agent be soluble within the propellant at temperatures ranging from about 0 degrees centigrade to about 43 degrees centigrade.

It is preferred that the amount of DPPC delivered upon each actuation of the administration device be from about 1 mg to about 10 mg. It is still further preferred that the amount of DPPC delivered be from about 1 mg to about 5 mg. It is still further preferred that the amount of DPPC delivered upon actuation be from about 2 mg to about 5 mg. Such dosages ordinarily provide the resultant decrease in eustachian tube opening pressure and associated increase in eustachian tube function as described above and below.

The administration housing utilized in practicing the first preferred method of the present invention contains a surfactant constituent and a propellant constituent. As discussed above, it is preferred, by not required, that the surfactant constituent be in a powdered form insoluble within the propellant constituent. It is so preferred so as to enable the formation of a colloid in which the crystalline form of the surfactant remains in the collimates stream administered by the device. The two constituents may be contained within an integral section of the device, such as a central bore of the canister containment section, without the need for or use of a separate canister bottle. However, the cannister containment section may also house a separate canister bottle which, for example, may comprise a metal cannister fitted with a valois metered dose valve. Upon activation of either the cannister housed within the administration housing or a valve within an administration housing having an integral mixture chamber, a mixture of the powdered surfactant and propellant exit the cannister, flow through conduits within a docking port of the delivery nozzle section and exit from the device as a collimated stream formed within the delivery nozzle.

In certain preferred embodiments of the present invention, canisters fitted with metered dose valve are utilized so that a selected and uniform amount of surfactant is delivered with each actuation. However, the surfactant may also be contained in other metered and non-metered dose canisters so long as such canisters are capable of providing, upon actuation, a stream of surfactant, capable of flowing through and being delivered by the device, as described, within the '366 application. For this purpose, pressurized canisters capable of delivering contents contained therein without a metered dose chamber and valve, as well as canisters which deliver their contents via a pump/pressurized air mechanism may equally be utilized with the present invention. As mentioned above, the canisters utilized may also be integrated as a continuous part of the administration housing. It is also contemplated that the device of the present invention may be utilized with surfactant contained within "blister packs", the contents of which are propelled through the device by a liquid propellant, compressed gas, or pump actuation utilizing atmospheric air.

All embodiments of the method of the present invention reduce the amount of surfactant required upon actuation of the device utilized as compared to the prior art discussed above. More specifically, the method of the present invention, in all embodiments thereof, eliminates the wasteful scattering and certainly none targeting spray of the prior art. The methods of the present invention enable a surfactant/propellant or a surfactant/propellant/therapeutically active agent to reach and enter the eustachian tube's nasopharyngeal orifice—without need of a spreading agent. However, once deposited at the eustachian tube orifice, the very same mucopolysaccharides that may cause eustachian tube dysfunction, now enhance spreading of the surfactant throughout the eustachian tube lumen and into the middle ear.

The second preferred method of the present invention provides a method for treating otitis media. The second preferred method can also be described, in certain embodiments, as a method for administering therapeutically active agents, effective in the treatment of otitis media, to the eustachian tube and middle ear chamber. In practicing the second preferred method, a collimated stream of a mixture of a dry powdered surfactant, a propellant and a therapeutically active agent is delivered to the stoma of the eustachian tube via an eustachian tube targeting delivery device. It is preferable, but not required that the surfactant constituent and the therapeutically active agent constituent be in a powdered form and not be soluble within the propellant. In this way, rather than forming a solution, the mixture delivered to the eustachian tube is in the form of a colloidal suspension. As mentioned above in regard to the first preferred embodiment, the mixture of a surfactant constituent and propellant constituent alone is effective in the treatment of otitis media by enhancing eustachian tube patency which enable the drainage of the middle ear provided thereby—even without incorporation of a therapeutically active agent. However, certain preferred embodiments of the second preferred method include a therapeutically active agent within the delivered mixture (disclosed, in detail, below) in order to provide further resolution of otitis media by treating the disease process itself through the action of antibiotic, antiviral, anti-inflammatory and other therapeutic agents.

The surfactant utilized in practicing the second preferred embodiment of the present invention is the same as disclosed above in regard to the first preferred embodiment. The propellant utilized in practicing the second embodiment is also the same as discussed above. As mentioned above, it is preferred, but not required, that the surfactant constituent and the therapeutically active agent constituent, form a colloidal suspension in the propellant constituent. More specifically, it is preferred that such propellant does not dissolve the surfactant and, when incorporated, therapeutically active agent at normal manufacturing, storage and delivery temperatures. More specifically, it is preferred that such constituents remain insoluble at a temperature range of from about 0 degrees centigrade to about 43 degrees centigrade. Also, it is preferred that the surfactant not be soluble at the range of physiologic temperatures encountered when the mixture is delivered to the nasopharyngeal orifice of the eustachian tube. Preferred propellants include fluorocarbon propellants in which, as discussed above, the lipid surfactant and therapeutically active agent may form a colloidal suspension. The fluorocarbon propellants may be advantageously selected to be chlorofluorocarbon propellants, hydrofluorocarbons or mixtures thereof. In addition, the present invention contemplates carbon dioxide as a suitable propellant. In addition, compressed air may be utilized.

In practicing the second preferred method of the present invention, upon administration—in the same manner as the first preferred method—, the propellant is evaporated from the mixture and the lipid surfactant crystals and therapeutically active agent, are deposited at a nasopharyngeal, (or as it may also be described, the stoma or anterior terminus) of a subject mammalian eustachian tube whereupon the lipid crystals come into contact with lumen surfaces of the tube. Because the mixture of lipid surfactant crystals and propellant are delivered via an eustachian tube targeting administration device, the mixture is directed towards the eustachian tube stoma. Upon contact with the mucosal lining of the eustachian tube lumen—and the air/liquid interfaces resident thereupon, the lipid surfactant crystals form an amorphous spread film effectively decreasing the opening pressure of the lumen. Mucoproteinaceous secretions also resident upon the epithelial lining, act as a natural spreading agent assisting the movement of the lipid surfactant and therapeutically active agents along the surface of the entire eustachian tube lumen and on to the epithelial lining of the middle ear. Although mucoproteinaceous secretions are always, to a degree, present within the eustachian tube lumen, the amount of such secretions dramatically increases during bouts of otitis media as well as upper respiratory infections and allergies. These secretions, which would otherwise increase the surface tension of the lumenal epithelial surfaces and interfere with opening of the lumen, in the presence of the lipid surfactant, actually assist the surfactant spreading throughout the lumen and reducing opening pressure thereof. Such action enables the eustachian tube to both perform normal pressure equalizing functions for the middle ear as well as enabling the lumen to drain infectious and inflammatory products produced during episodes of otitis media so as to speed the resolution thereof.

In practicing the second preferred method of the present invention, in addition to utilizing a mixture of a powdered surfactant and propellant, a therapeutically active agent, effective in the treatment of otitis media in certain embodiments, is incorporated. Therefore, in certain preferred embodiments, the second preferred method of the present invention provides a method of administering therapeutically active agents directly to lumen surfaces of mammalian eustachian tubes, and also, by means of said eustachian tube lumen, to the middle ear chamber and the tissues therein. Once delivered to these tissue, the therapeutically active agents provide effective treatment for otitis media while, in addition, providing the same increased eustachian tube patency and performance as the first embodiment.

The therapeutically active agent is advantageously selected to be effective in the treatment of otitis media as well as agents effective in the treatment of the underlying causes thereof which provoke the related immune responses leading to the above-described inflammatory responses.

BRIEF DESCRIPTION OF THE DRAWINGS

Detailed Description

Figure 1:
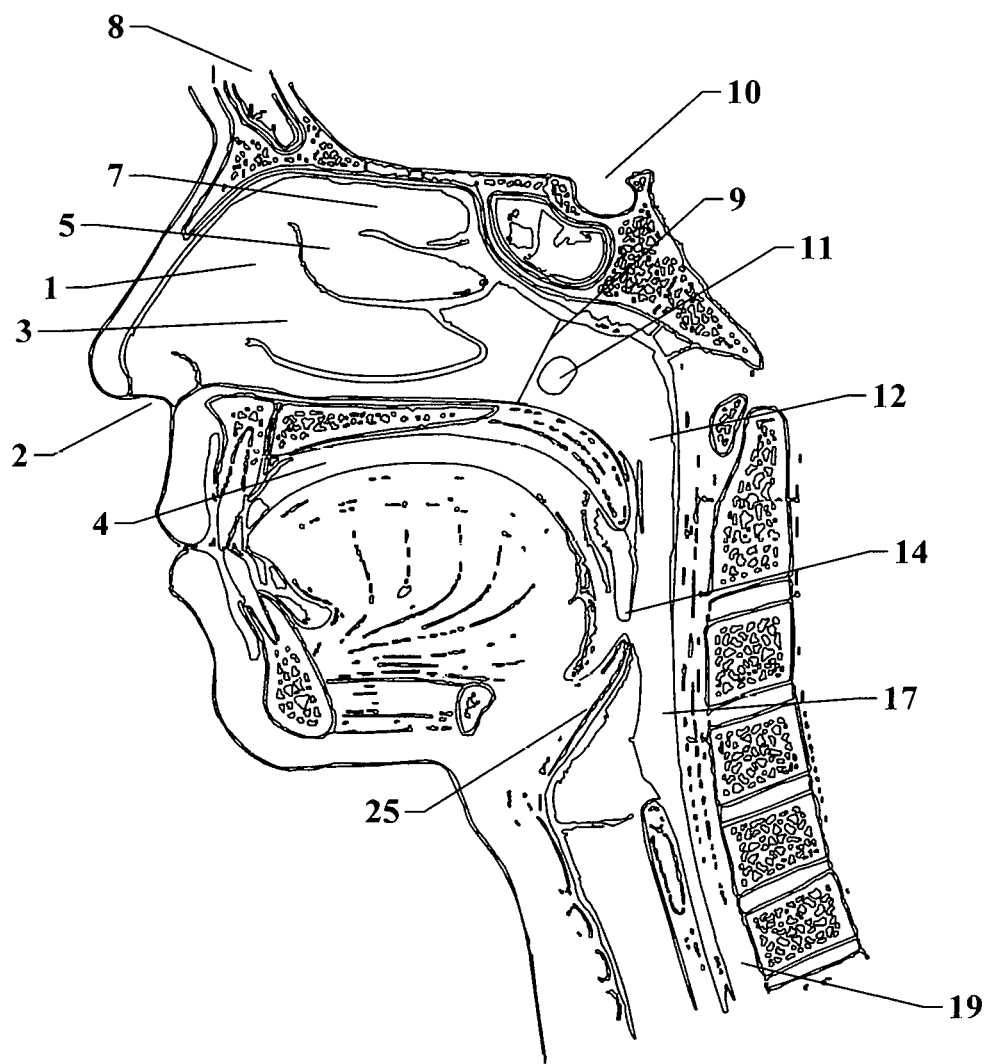

FIG. 1 is a detailed lateral internal partial view of a human head illustrating internal structures of the oral, nasal, pharyngeal and tracheal areas therein.

Figure 2:
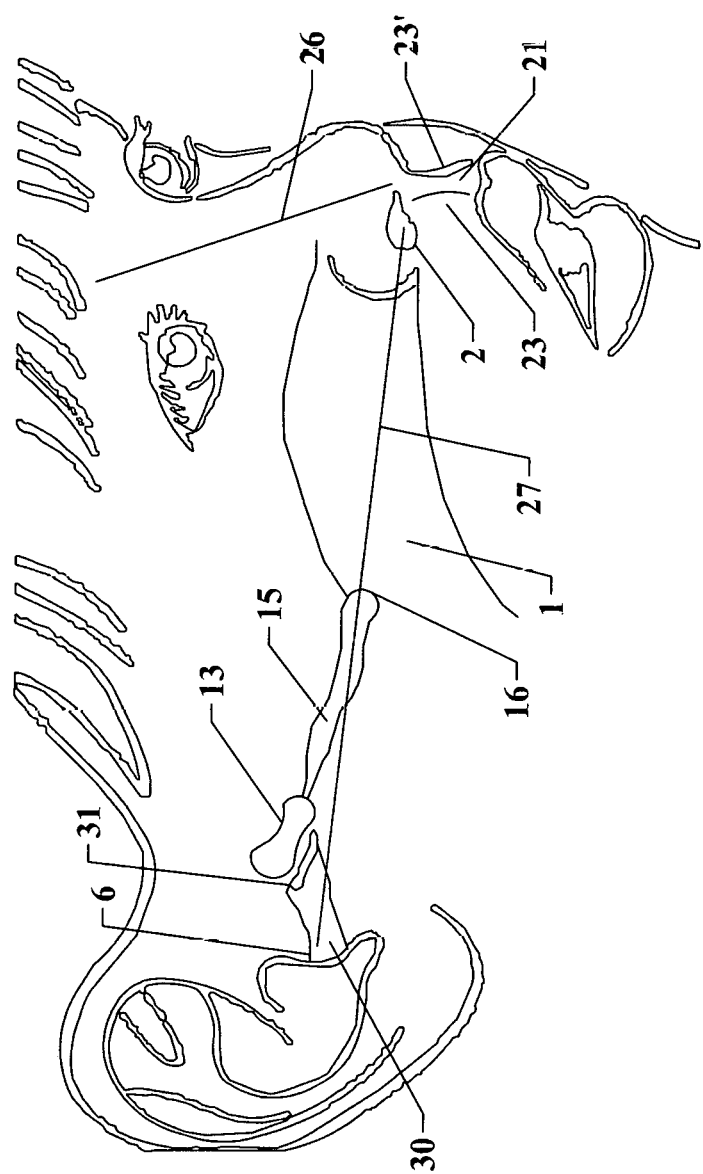

FIG. 2. is a lateral view of a child's face illustrating internal relationships of the nostril, nasal cavity, nasal pharynx and eustachian tube.

Figure 3:
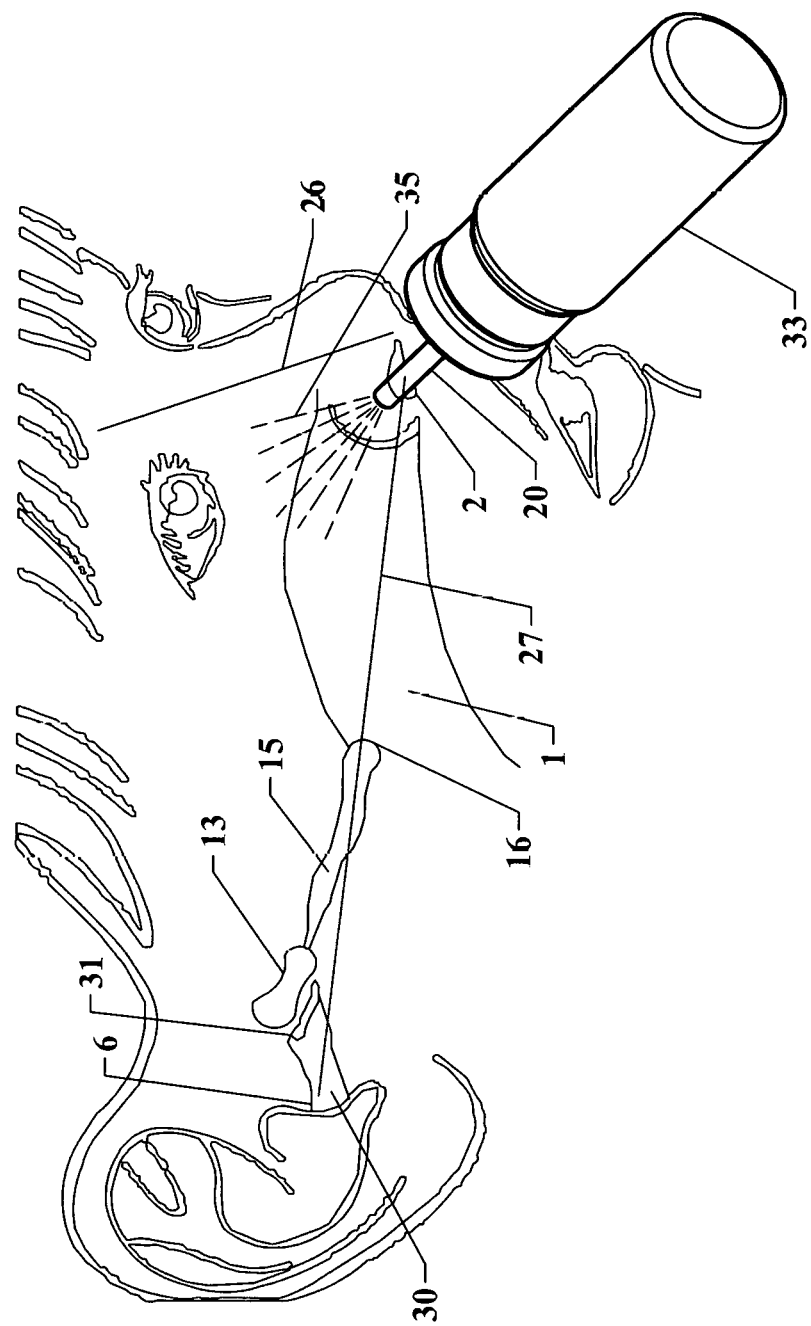

FIG. 3 is the lateral view of the child's face shown in FIG. 2 with a prior art nasal delivery device in place and activated.

Figure 4:
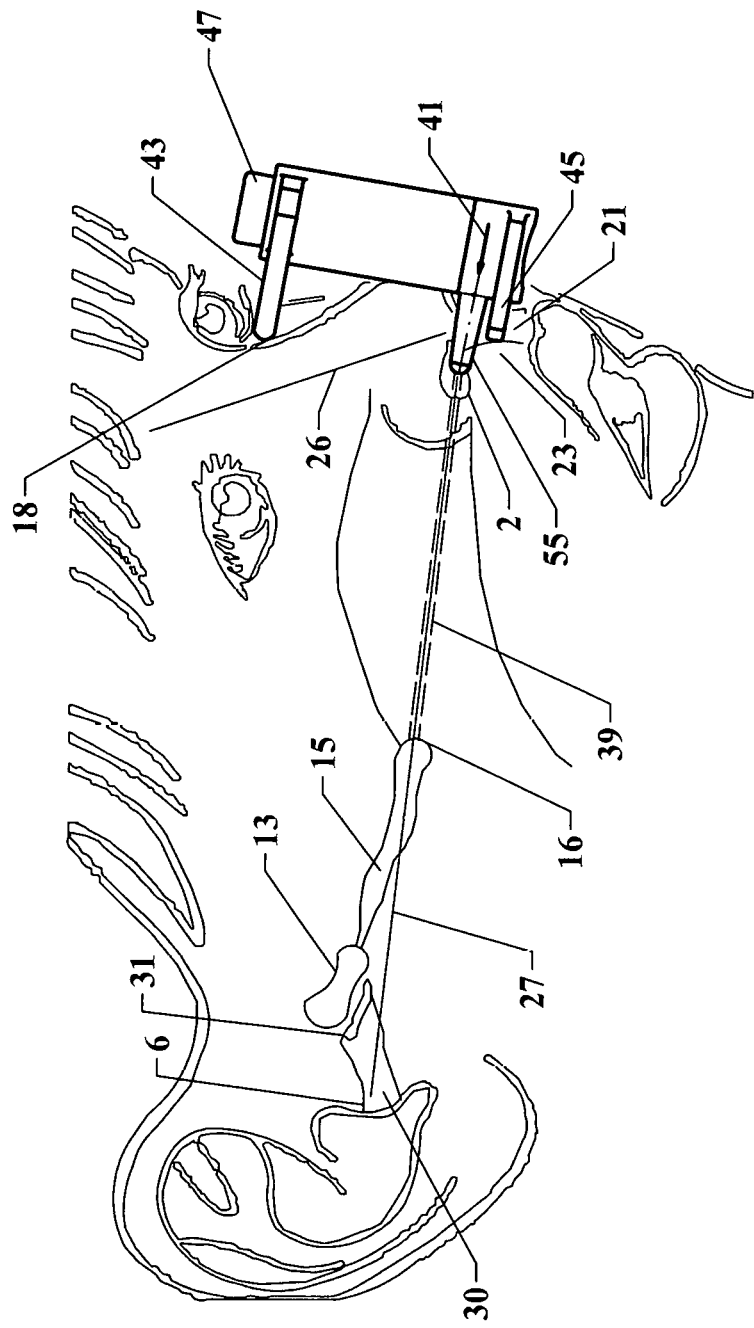

FIG. 4 is a lateral view of the child's face shown in FIG. 2 with an eustachian tube targeting nasal administration device which can be utilized in practicing the present method in place and activated.

Figure 5:
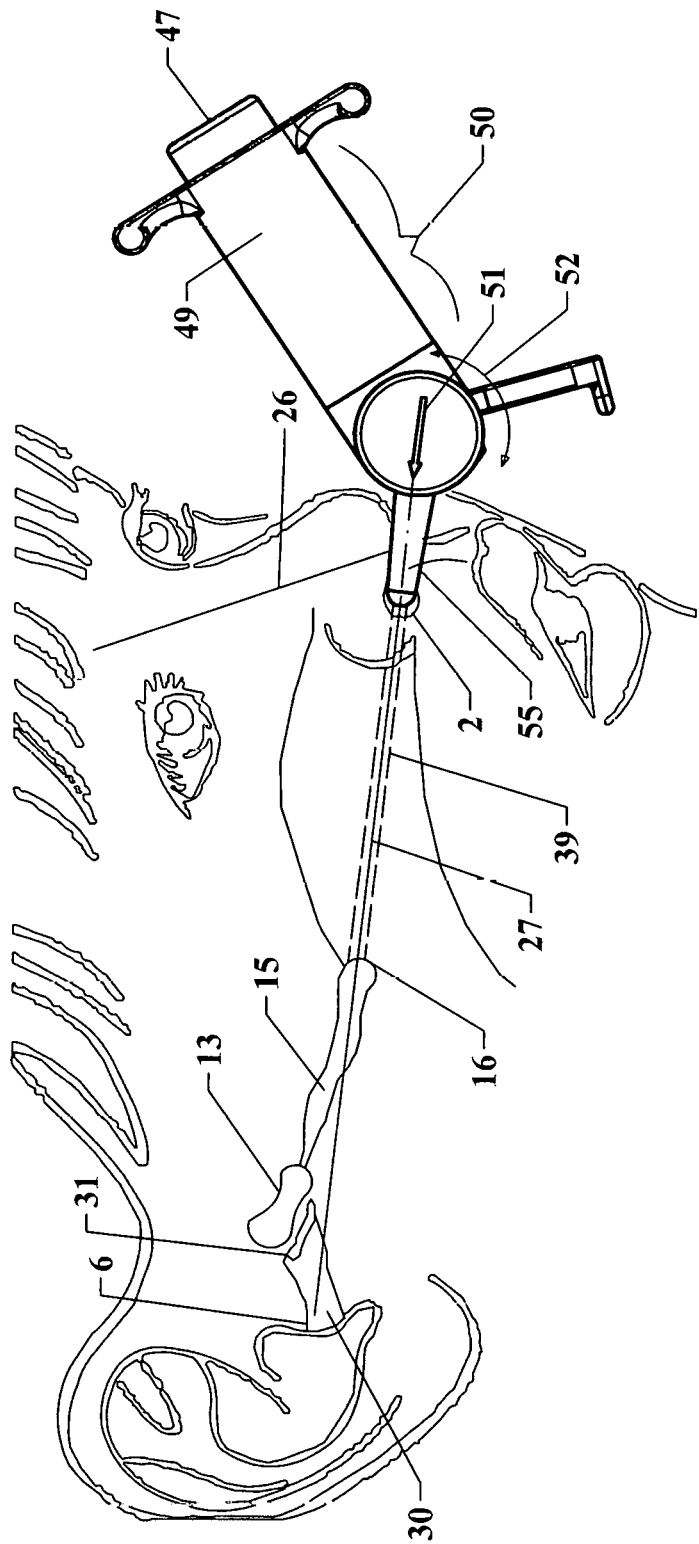

FIG. 5 is a lateral view of the child's face shown in FIG. 2 with an alternate embodiment of an eustachian tube targeting nasal administration device which can be utilized in practicing the present method in place and activated.

Figure 6:
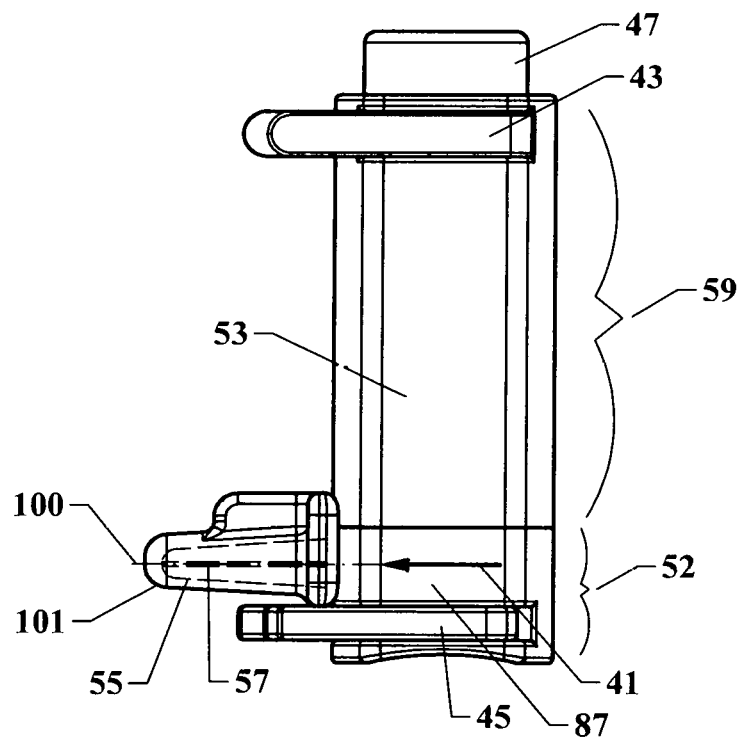

FIG. 6 illustrates a side view of an eustachian tube targeting administration device which can be utilized in practicing the method of the present invention.

Figure 7:
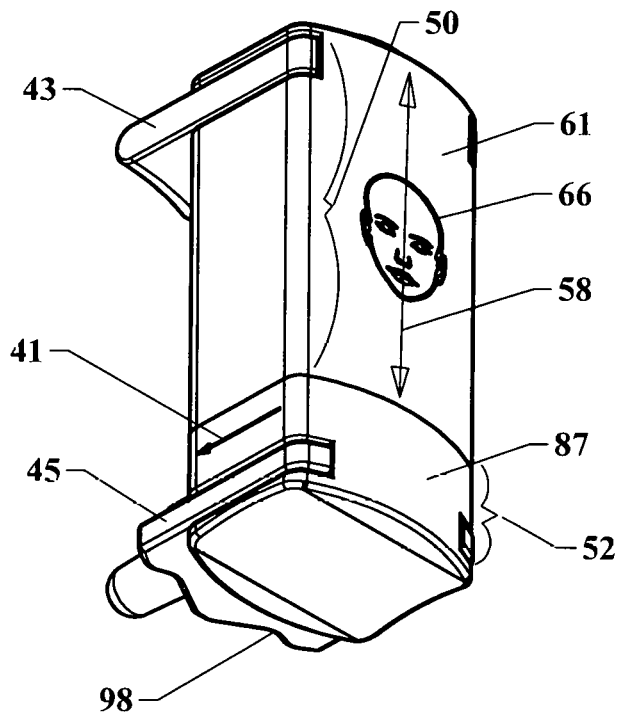

FIG. 7 illustrates a bottom rear isometric view of the device illustrated in FIG. 6.

Figure 8:
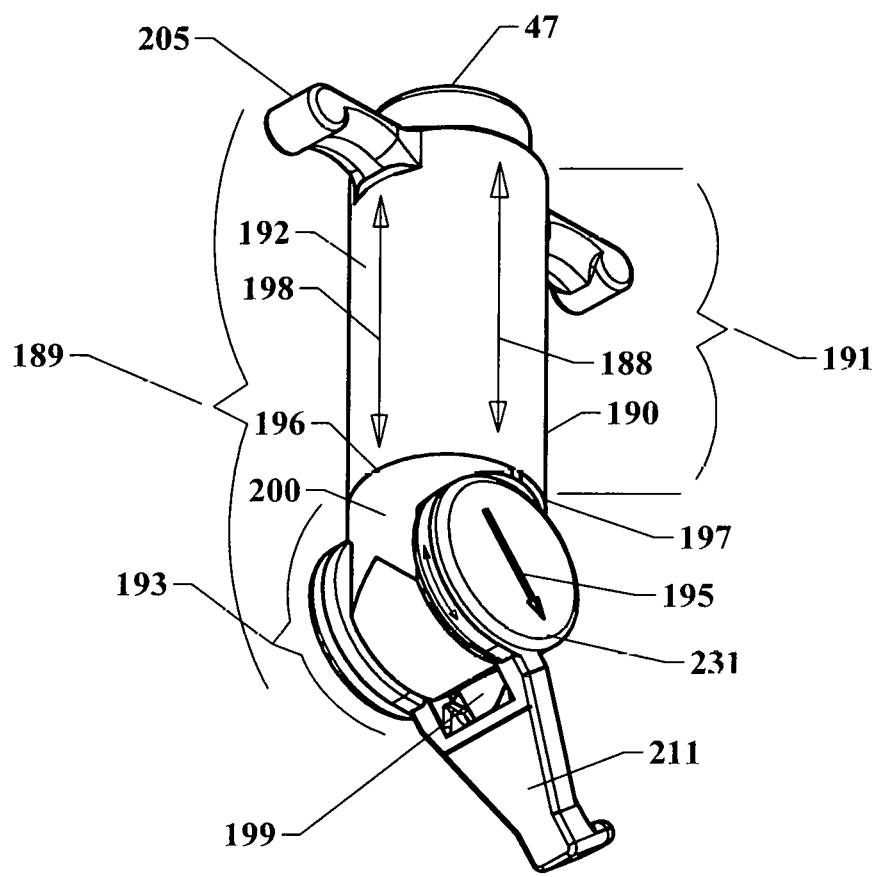

FIG. 8 illustrates a bottom rear isometric view of an alternate embodiment of an eustachian tube targeting administration device which can also be utilized in practicing the method of the present invention.

DETAILED DESCRIPTION

As described above, the methods of the present invention enables the effective use of a simplified medication—a mixture consisting of a surfactant constituent and a propellant constituent—without need of a spreading agent—in order to enhance eustachian tube function and as a treatment for otitis media.

As shown, in detail, in FIG. 1, each nostril 2 of a human subject leads to the nasal cavity 1 which, like adjacent spaces such as, for example, the nasopharynx 12, the ethmoid sinuses 10, and the frontal sinuses 8 is lined with an epithelial mucosa. All of these mucosal services have an air/liquid layer resident upon the mucosal lining thereof. The nasal cavity 1 includes inferior 3, middle 5 and superior 7 turbinates which are also covered by the mucosal surface described immediately above. The nasal cavity is separated, by means of the hard palate, from the oral cavity 4. The oral cavity, at its posterior terminus leads to the oral pharynx 14.

The nasal cavity is divided, bilaterally, into a right and left segment by the nasal septum. The nasal septum ends, posteriorly, at the choanae 9 which includes to openings leading from the left and right portions of the nasal cavity to the nasopharynx 12, which lies just posterior (dorsal) to the nasal cavity. Within the nasopharynx lies a right and left nasopharyngeal opening (stoma) of the eustachian tube 11. As mentioned above, the eustachian tube, which is normally a closed, flattened structure, regularly opens for pressure equalizing functions (between the middle ear and atmospheric pressure at the nasopharynx), as well as to serve as a drain for fluids that build up in the middle ear during, for example, infections and inflammatory events which can occur during otitis media. The opening of the cental lumen of the eustachian tube enables such fluids to drain out of the middle ear, eustachian tube and then enter, and travel down through the nasopharynx 12, oral pharynx 14 and laryngopharynx 17 pharynx, and, thereafter, through the esophagus 19 for elimination through the remainder of the digestive system. The opening function of the eustachian tube lumen is compromised when the air/liquid interface resident upon the mucosal lining of the eustachian tube lumen undergoes an increase in surface tension caused by a change from a thinner serous fluid to a coating demonstrating a higher percentage of mucoproteins/mucopolysaccharides. More specifically, this thicker coating secreted upon the mucosal lining of the auditory tube lumen greatly increase the surface tension of the mucosa. This increased in surface tension increases the attraction of opposing walls of the lumen so as to greatly increase the amount of pressure necessary to open the lumen for function (referred to herein, an throughout the art, as "opening pressure").

The present invention provides a method of improving eustachian tube function by directing a mixture consisting of a surfactant constituent and propellant constituent directly towards the nasopharyngeal eustachian tube orifice. It achieves this goal, without the delay otherwise necessitated by the indiscriminate application of a surfactant/spreading agent combination when a prior art nasal application device is utilized. Simply put, by utilizing a eustachian tube targeting nasal administration device as described in more detail, below, and, and as illustrated in FIGS. 5 and 6, a concentrated and targeted delivery of surfactant/propellant is delivered directly towards the naso-pharyngeal orifice of the eustachian tube—without need to migrate from the far reaches of the nasal cavity pharynx and other adjacent areas—discussed above and illustrated in FIG. 1.

As illustrated in FIG. 2, there is a pathway that leads directly from a patient's nostril 2 to the eustachian tube opening 16 located on the same side of the patient's face (and nasal septum) as the nostril entered. This pathway, or, as it may also be referred to, the nasal/tragus elevation reference line 27. This reference line runs from a patient's nose to the tragus of the patient's ear on the same side of the face as nostril entered. This elevation reference line intersects, along it traverse, the nasopharyngeal opening of the eustachian tube. Thus, when, as mentioned above, a collimated stream of surfactant is administered through a patient's nostril on an elevational pathway which is in line with the tragus 6 of the patient's ear on the same side of the patient's face as the nostril entered, the collimated stream of surfactant will target the aforementioned opening of the eustachian tube and thereafter enter into the lumen of the eustachian tube 15. Once the surfactant/propellant mixture enters the eustachian tube orifice, it quickly reduces the surface tension causing the tube to remain closed, and thereby forms a patent pathway from the middle ear cavity 13. The middle ear, without access to a patent eustachian tube, is effectively sealed off and thus prevented from providing drainage and pressure equalization through the external ear canal 30 by the tympanic membrane 31.

The above-described targeting function of the administration device utilized in the methods of the present invention is accomplished by means of the devices disclosed, taught, illustrated and claimed within U.S. patent application Ser. No. 15/530,366.

FIG. 3 illustrates a nasal administration device of the prior art 33. The nozzle 20 of the device releases a indiscriminate spray 35. The illustrated device, in common with all prior art devices, has no means of specifically targeting or otherwise directing compounds delivered thereby to the eustachian tube orifice 16 or, for that matter, any other particular target tissue. Compounds released from such a device can reach the mucosa of the nasal cavity, including the inferior, middle and superior turbinates, as well as the mucosa of the nasal floor and ceiling but are generally directionless applicators 35. Even if such devices are fitted with a nozzle that provides a narrow stream, no prior art nasal administration device incorporates a means for aligning such a stream with the auditory tube orifice. The compounds administered by prior art devices may also be inadvertently administered in the direction of adjacent nasal, oral, pharyngeal and sinus spaces. Thus, the nasal administration device of the prior art, devoid of any targeting means, require the use of a surfactant, in combination with a spreading agent, in order to allow even a portion of the surfactant to reach the eustachian tube. Since such devices deposit surfactant over a wide and indiscriminate area, a spreading agent, which enables the mixture to more rapidly spread over the entire mucosal lining of the nasal cavity, nasopharynx and adjacent sinuses, assures that—at least a portion of the surfactant—will eventually reach the stoma 16 of the eustachian tube. After traveling along the mucosa of adjacent structures and reaching the stoma a small portion of surfactant is then able to enter the lumen of the eustachian tube 15 and eventually reach the middle ear 13.

FIG. 4 illustrates the use of an example of a eustachian tube targeting nasal administration device used in practicing the method of the present invention. The device includes an administration housing which includes a cannister alignment tab 43 which enables stable positioning of the device upon the bridge portion 18 of a patient's nose. The particular embodiment illustrated also includes a delivery section alignment tab 45 for stable placement of the device upon the philtral column 23 on the side of the nose as the nostril 2 entered by the collimation, or, as it may also be referred to as, the delivery nozzle 55. With the administration device so positioned as stabilized, the shape, dimensions and configuration of the housing caused, upon activation, a stream of surfactant/propellant mixture, derived from cannister 47 consisting of a surfactant constituent and a propellant constituent (housed within the device), to form a collimated stream 39 within the collimation nozzle 55 and follow a pathway aligned with the nasal/tragus elevation alignment line 27 so as to direct the mixture directly towards the eustachian tube orifice 16. To prevent medial or lateral diversion of the collimated stream, the longitudinal axis of the housing is aligned with the midline of the patient's face during positioning and activation. Once the surfactant/propellant mixture reaches and enters the eustachian tube orifice 16 the surfactant acts to lower the surface tension of secretions coating the lumen 15 of the eustachian tube and on to mucosa lining the middle ear chamber 13. The surfactant/propellant mixture contained within the device is free of, and does not require a spreading agent due to the directed delivery of the mixture towards the eustachian tube stoma.

FIG. 5 illustrates an alternate embodiment of an eustachian tube targeting nasal administration device 49 useful in practicing the methods of the present invention. A cannister 47 containing a mixture consisting of a surfactant constituent and a propellant constituent, is contained within the cannister containment section 50 of the device. A delivery nozzle 55 having a longitudinal axis, demonstrates a constant, continuous diameter enabling the nozzle to deliver a well collimated stream of surfactant/propellant 39 which is released upon activation of the device. The device is provided with a nostril/tragus elevation alignment line/arrow 51 formed within or upon the sides of the delivery nozzle section 52 in such a position and orientation so that the elevation alignment line/arrow is in parallel alignment with the longitudinal axis of the collimated stream 39 released from the delivery nozzle. Therefore, by inserting the delivery nozzle of the device 55 within the nostril 2 of a patient, while, at the same time, positioning the device so that the nostril/tragus elevation alignment line/arrow 51 is pointing towards the tragus 6 of the patient's ear (on the same side of the patient's face as the nostril entered), the collimated stream released from the delivery nozzle upon device activation is directed towards, so as to target the nasopharyngeal orifice 16 of the eustachian tube 15. In addition, the device is also positioned so that the midline alignment line formed within or upon the back surface of the device is aligned with the midline 26 of the patient's face so as to prevent lateral or medial deviation of the collimated stream of surfactant/propellant from the eustachian tube orifice. Upon delivery of the surfactant/propellant mixture, the surfactant enters the liquid/air interface resident upon the mucosal surfaces of epithelium lining the eustachian tube lumen 15 through which the surfactant reaches the mucosal surfaces of the middle ear 13. Targeted delivery of the surfactant/propellant speeds the onset of the surface tension/opening pressure reduction effect provided by the surfactant. In the second preferred method of the present invention wherein, in addition to a surfactant/propellant mixture, a therapeutically active agent is included, the method of the present invention also delivers such agents more rapidly to the target tissues of the eustachian tube and middle ear as compared to prior art methods which utilized non-directed, non-targeting application. Therefore, the methods of the present invention provide more rapid resolution of otitis media by providing enhanced speed of delivery of both surfactant and therapeutic agent to target tissue.

FIGS. 6 and 7 illustrate an example of a preferred eustachian tube targeting nasal administration device 53 especially useful for practicing the method of the present invention. The device, in common with all examples illustrated, includes a cannister containment section 59 as well as a delivery nozzle section 52. The cannister containment section houses a cannister 47 containing a surfactant constituent and a propellant constituent as a mixture within a central bore thereof. When practicing the second preferred method of the present invention, a therapeutically active agent is also included in the mixture. In certain embodiments, the eustachian tube targeting nasal administration device advantageously includes a cannister containment section alignment tab 43 is located towards the upper/superior terminus of the cannister containment section and is utilized, as described above, to stabilize and position the device against the bridge portion of a patient's nose. In certain examples of this embodiment, the alignment tab 43 may be adjustable in regard to extending away and withdrawing back towards the front surface of the device which ordinarily faces the patient and from which the delivery nozzle depends. Certain embodiments of this delivery device also include a midline alignment line 58 formed upon the back surface of the device and positioned in the middle of the back surface in alignment with the longitudinal axis of the central bore of the cannister containing section. Certain examples of this device include a pictograph of a face 66 with the midline alignment line superimposed along the midline of the face image as guidance measure for users thereof. The delivery nozzle section 52 of the device matingly attaches to the inferior terminus of the cannister containment section in such a manner as to enable a cannister, housed within the device to mate with a cannister docking station located within the delivery nozzle section. The docking station includes conduits providing a fluid connection between the cannister valve stem engaged by the docking station and the delivery/collimation nozzle 55 mounted upon the front surface of the delivery nozzle section. The delivery nozzle includes a central bore—having a longitudinal axis 100—as well as openings on its proximal and distal termini all in fluid communication with the aforementioned conduits formed within the docking station. The diameter of both of the aforesaid openings on the proximal and distal termini of the delivery nozzle and the central bore 57 thereof are equal and continuous in order to provide the collimated stream. The precise diameter of the bore and openings is selected in accordance with the surfactant/propellant mixture within the cannister so as to attain enhanced collimation.

A delivery nozzle adjustment tab 45 may, in some embodiments, be provided in order to provide further adjustability of the position of the device. However, in all embodiments, the device is positioned for use, as described above, so that the longitudinal axis 100 of the delivery nozzle 55 is aligned with the nostril/tragus elevation line, a reference line running from the patients nostril to the tragus of the ear on the same side of the patient's face as the nostril entered by the nozzle. For this purpose, the side surfaces 87 of the delivery nozzle section 52 include, in certain preferred embodiments, a nostril/tragus elevation alignment line/arrow 41 which, as in all embodiments having such, is in parallel alignment with the longitudinal axis 100 of the collimation/delivery nozzle. Therefore, the collimated stream of surfactant and propellant which are released from the distal opening of the nozzle will be aligned with the nostril/tragus elevation reference line when the device is positioned so that the elevation alignment line/arrow points to the tragus of the patient's ear when the nozzle is inserted into the nostril on the same side of the patient's face as the tragus. An optional nozzle cap 101 may be provided in order to protect and keep from contamination the nozzle when not in use.

FIG. 8 illustrates an alternate embodiment of an eustachian tube targeting nasal administration device disclosed within the '366 application which is advantageously utilized in practicing all of the preferred methods of the present invention which (as illustrated, in use, in FIG. 5.) Although this eustachian tube targeting nasal administration device is especially useful in practicing the methods of the present invention upon infants and non-compliant patients, this device may also be used, with equal effect, upon any human patient, regardless of age or compliance. This eustachian tube targeting nasal administration device incorporates an administration housing comprised of a canister containment section 191 and a delivery nozzle section 193 devoid of the alignment tabs discussed above, but inclusive of an elevation alignment line/arrow 195 that is formed upon or within the side surfaces of the delivery nozzle section in alignment with the longitudinal axis of the collimation nozzle and the stream of medicine that is projected therefrom. The elevation alignment line/arrow enables a user to rapidly and correctly orient the device for proper direction of a surfactant/propellant stream towards the pharyngeal opening of the eustachian tube.

The canister containment section 191 of the housing is a simple, hollow tube, having a longitudinal axis 188, especially shaped and configured to contain and securely retain a canister 47 containing a surfactant constituent and a propellant constituent. In practicing the second preferred method of the present invention, a therapeutically active agent constituent is also included, as discussed in more detail above and below. As mentioned above, the canister utilized may be a pressurized canister utilizing a propellant—in liquid or gas form—or such canister may simply incorporate a mechanical pump for directing the surfactant/propellant mixture. In still further embodiments, the canister containment section itself serves as the container for the mixture without need of a separate canister. The canisters utilized include metered dose canisters utilizing liquid, gas or a combination of same as a propellant. In the embodiment illustrated in FIG. 8, the canister containment section includes a front portion 190, a rear portion 192, a superior terminus 194 and an inferior terminus 196. The superior terminus 194 is open which enables passage therethrough of a canister bottle. The inferior terminus 196 of the canister containment section is especially shaped and configured to mate with and engage the delivery nozzle section 193 discussed below. The containment canister section may advantageously demonstrate a length slightly less than the length of the canister bottle so as to enable a small portion of the distal end of the canister to extend beyond the canister containment section so as to allow access to depress the bottle for actuation of the metering valve and release of canister's contents. The canister containment section also includes two finger rests 205 extending from the front and back portion of the section adjacent to the proximal terminus thereof located approximately opposite one another (in a 180 degree relation). The finger rests provide, as discussed below, a means of holding and quickly manipulating the position of the device during use as well as finger holds to bias against when depressing the distal end of the canister bottle with, for example, an additional finger during operation of the device. Centered upon the rear portion of the canister containment section 192 of the housing a midline alignment mark 198 is provided running parallel to the longitudinal axis 188 of the canister containment section. When utilizing this device in practicing the method of the present invention, the device is oriented so that the midline alignment mark faces away from the patient's face, as shown in the figures, and parallel to the midline of the face, so that the collimation nozzle is oriented directly into the plane of the patient's face. The delivery nozzle section 193 of the administration housing defines a short hollow cylinder having two side surfaces, a front surface 197 and a back surface 200. The delivery nozzle section of the administration housing also demonstrates a superior terminus especially shaped and configured to matingly engage the inferior terminus of the canister containment section. The delivery nozzle section further demonstrates a rounded closed inferior terminus and a central bore especially configured and adapted to contain a docking port. In certain examples of this alternate embodiment, a rotating delivery nozzle cover 211, as described below, is provided.

The delivery nozzle section of the alternate embodiment of the targeting nasal administration device includes a nozzle port located on the front surface thereof adjacent to the inferior terminus. The nozzle port is especially configured and adapted for secure engagement of the collimation nozzle described above. The nozzle port is positioned upon the barrel shaped portion of the nozzle section so that it arises from the front surface of the device and opposite the rear surface midline alignment mark discussed above. This configuration enables a user to position the device so that the midline alignment mark appears centered on the back surface of the device is in parallel alignment with the midline of the patient's face during device activation. This positioning assures that the collimated stream administered by the device is applied directly into the plane of the patient's face without lateral or medial deviation. Such alignment, along with aligning the device in accordance with the elevational alignment line/arrow with the tragus of the patient's ear, provides excellent targeting of the pharyngeal opening of the eustachian tube.

In practicing the second preferred method of the present invention, a therapeutically active agent is included within the mixture of the surfactant constituent and the propellant constituent. Within the middle ear chamber, as well as within the lumen of the auditory tube, the therapeutically active agent acts to resolve causative infections as well as inflammation and/or congestion associated with otitis media. At the same time, the surfactant constituent exerts a physical chemical change within the lumen of the eustachian tube by lowering the surface tension thereof to achieve and enhance eustachian tube patency. In contrast, the therapeutically active agent treats the underlying causes and inflammatory effects of otitis media. The therapeutically active agent is advantageously selected to be effective in the treatment of otitis media as well as agents effective in the treatment of the underlying causes thereof which provoke the related immune responses leading to the above-described inflammatory responses. For example, such agents may be selected to be effective in the treatment of mycotic, viral or bacterial infections, (as well as combinations thereof) underlying and causative of said inflammatory reactions. Therefore, the second preferred method of the present invention provides a method of administering therapeutically active agents directly to the epithelial lining of the eustachian tube and the middle ear chamber wherein said therapeutically active agents provide effective treatment for the subject inflammatory condition such as, for example edema as well as the underlying causes thereof. The therapeutically active agent may be, for example, an anti-inflammatory, antibiotic, antiviral, decongestant, gene therapy agent or mixtures thereof. The anti-inflammatory agent may be betamethasone including, for example, betamethasone dipropionate and betamethasone valerate as well as all other effective formulations. The de-congestive agent may be selected to be phenylephrine, including, for example, phenylephrine HCL and phenylephrine bitartrate and all other effective formulations thereof. The antibiotic selected may be, for example, erythromycin, amoxicillin, zythromax, and augmentin (amoxicillin and clavuliic acid) in all of their effective formulations and gene therapy agents. Gene therapy agents, as the term is used herein, refers to a biochemical substance—as well as vectors thereof—selected from the group including, but not limited to, proteins, peptides or amino acids; nucleic acids such as DNA, including full length genes or fragments thereof derived from genomic, cDNA, or artificial coding sequences, gene regulatory elements, RNA including mRNA, tRNA, ribosomal RNA, ribozymes and anitsense RNA, oligonucleotides, oligoribonucleotides, deoxyribonucleotides and ribonucleotides as such agents may exist as isolated and purified compounds or in unpurified mixtures, such as tissue, cell or cell lysate. In addition, such agents may be naturally occurring, synthetic, or a mixture thereof. The term "all of their effective formulations" as used throughout this specification and in the claims refers to those specific species of a particular therapeutic agent effective in the treatment of otitis media.

As discussed above, in practicing the methods of the present invention, the surfactant constituent is selected from cholesteryl esters, phospholipids, carbohydrates, and proteins, all in powder form. However, it is preferred that said surfactant be selected to be a phospholipid, and still further preferred that said phospholipid be selected to be of the class phosphatidlycholine including any fully saturated diacyl phosphatidlycholine including 1,2 dipalmitoyl phosphatidylcholine (DPPC).

In regard to DPPC, the preferred surfactant constituent, It is preferred that this surfactant be in a dry powdered form demonstrating a particle size of from about 1 to about 50 microns. It is still further preferred that the surfactant demonstrate a particle size of from about 5 to about 40 microns. It is still further preferred that the powdered surfactant demonstrate a particle size of from about 1 to about 15 microns as such a size distribution minimizes the occurrence of valve clogging and enhances consistent dosage by providing a more uniform mixture.

Example: Preparation, Bottling, Concentration and Dosage

DPPC was obtained from Avanti Polar Lipids, Alabaster Alabama. It is prepared to a final, dry form by evaporation from organic solvents. The final, dry form of DPPC is then combined with the preferred propellant HFA134a to form a colloidal mixture.

The mixture is prepared in 19 mL canisters fitted with either 100, 75 or 50 microliter Bespak metering valves. Depending on the aerosol dose required, the concentration of the HFA134a propellant/DPPC suspension can be varied with the metering valve. For example, to deliver a collimated stream containing a preferred dose range of from about 2.5 to about 3.5 mg of DPPC per valve actuation utilizing a 19 ml cannister—fitted with a 100 micro-liter valve—, a 2.5-3.5% Active Pharmaceutical Ingredient (API) concentration is utilized. In order to achieve this same dose (providing a collimated stream containing 2.5 to about 3.5 mg per actuation) utilizing a metered dose cannister fitted with a 75 micro-liter valve, a 3.3-4.6% API concentration is utilized. A 19 ml metered dose cannister fitted with a 50 micro-liter valve would require a 5.0-7.0% API concentration in order to achieve this same dose per actuation.

Example: Manufacturing Considerations

For a manufacturing run of 300 cans a pressure vessel is filled with 160 grams of dry powder DPPC and 7.2 Kg of HFA134a propellant and mixed. The 100 microliter Bespak metering valves are crimped onto 19 mL cans and the cans then filled from the pressure vessel by recirculating the mixture through the vessel to the 18.3 gram fill weight. This delivers a dose of 3 mg—per spray—of DPPC.

This provides a repeatable dose with a homogeneous spray.

The DPPC prepared as described within these examples is easily assayed with HPLC, whereas the combination mixtures of the prior art which required spreading agents necessitate additional assays to determine amounts of each of the constituents in each dose. The formulations of the prior art which utilized the addition of the spreading agent also lead to agglomeration and clumping of the constituents causing varying ratios of the compounds from dose to dose, as well as an effect on the total amount of the dose delivered er spray. This aggregation will lead to clogging of the actuator.

As discussed above, in practicing the methods of the present invention, the propellant may be advantageously selected to be fluorocarbon propellant such as, for example, chlorofluorocarbon propellants, hydrofluorocarbons or mixtures thereof. Carbon dioxide, as well as pressurized air may also be utilized as the propellant. In fact, the propellant may be any pharmaceutical grade, hypo-allergenic propellant. It is preferred that the surfactant be in a powdered form and not be soluble within the selected propellant as discussed above. In those embodiments of the present invention wherein a therapeutically active agent is also incorporated into the mixture, it is also preferred that such active agent also be in a powdered form and also be insoluble within the propellant at the usual ranges of manufacturing, storage and physiologic application temperatures as discussed above. However, although the methods of the present invention prefer the use of propellants in which neither the surfactant and/or in the case of embodiments incorporating a therapeutically active agent, such agent(s) are also insoluble, the present method also contemplates embodiments where such constituents are soluble in a pharmaceutical grade propellant.

We claim:

1. A method for enhancing eustachian tube patency in a human patient utilizing an eustachian tube targeting nasal administration device wherein said device comprises an administration housing having a canister containment section and a delivery nozzle section, said method comprising:
    filling a canister with a selected mixture consisting of a selected surfactant constituent and a selected propellent constituent;
    inserting the canister with the selected mixture into the canister containment section of the administration device;
    positioning the device so that an alignment tab, depending from a front surface of the canister containment section, is placed in stable contact with a bridge portion of the patient's nose;
    positioning the device so that a delivery nozzle, depending from a front surface of the delivery nozzle section, having a central bore demonstrating a longitudinal axis and openings at a proximal and distal end in fluid communication therewith, is placed within and enters a nostril on a selected side of patient's face; and
    activating the canister so that a portion of the mixture of surfactant and propellant is released from the canister, flows through conduits formed within the delivery nozzle section and thereafter flows through the central bore of the delivery nozzle wherein, due to a uniform, constant and selected diameter of the openings located at proximal and distal ends thereof as well as the central bore of the delivery nozzle, forms and releases a collimated stream of the mixture from said distal opening;
    whereupon, due to the positioning, size, shape and configuration of the device, the collimated stream released by the delivery nozzle is directed towards a pharyngeal orifice of the eustachian tube thereafter the surfactant rapidly reaching and entering into a central lumen of the eustachian tube and lowering the opening pressure thereof.

2. The method of claim 1 wherein the surfactant constituent of the mixture contained within the canister inserted into the containment section is selected from the group consisting of cholesteryl esters, phospholipids, carbohydrates, and proteins.

3. The method of claim 1 wherein the propellant constituent of the mixture contained within the canister inserted into the containment section is selected from the group consisting of a fluorocarbon propellant, a chlorofluorocarbon propellant, a hydrofluorocarbons, carbon dioxide and compressed air.

4. The method of claim 2 wherein the surfactant constituent is selected to be a phospholipid.

5. The method of claim 4 wherein the propellant constituent of the mixture contained within the canister inserted into the containment section is selected from the group consisting of a fluorocarbon propellant, a chlorofluorocarbon propellant, a hydrofluorocarbons, carbon dioxide and compressed air.

6. The method of claim 5 wherein the surfactant constituent is selected to be 1,2 dipalmitoyl phosphatidylcholine.

7. The method of claim 6 wherein said method further comprises positioning the administration device so that an elevation alignment arrow, located upon side surfaces of the delivery nozzle section, points towards a tragus portion of an ear located on the same side of the patient's face as the nostril in which the delivery nozzle is placed and enters.

8. The method of claim 7 wherein said method comprises further adjusting the position of the nasal administration device so that a midline alignment line, located on a back surface of the canister containment section, is placed in parallel alignment with a midline of the patient's face.

9. The method of claim 1 wherein said method further comprises positioning the device so that a second alignment tab, extending from a front surface of the delivery nozzle section, is placed into stable contact with the patient's face just below the nostril in which the administration nozzle is placed and enters.

10. A method for enhancing eustachian tube patency in a human patient utilizing an eustachian tube targeting nasal administration device wherein said device comprises an administration housing having a canister containment section and a delivery nozzle section, said method comprising:
    inserting a canister containing a selected mixture consisting of a selected surfactant constituent and a selected propellent constituent into the canister containment section of the administration device;
    positioning the device so that a delivery nozzle, depending from a front surface of the delivery nozzle section, having a central bore demonstrating a longitudinal axis and openings at a proximal and distal end in fluid communication therewith, is placed within and enters a nostril on a selected side of patient's face;
    further positioning the device so that an elevation alignment arrow, formed upon side surfaces of the delivery nozzle section, points towards a tragus portion of an ear located on the same side of the patient's face as the nozzle was placed and entered;

activating the canister so that a portion of the mixture of surfactant and propellant is released from the canister, flows through conduits formed within the delivery nozzle section and thereafter flows through the central bore of the delivery nozzle and, due to a uniform, constant and selected diameter of the openings of the proximal end, distal end and the central bore of the delivery nozzle, forms and releases a collimated stream of the mixture from the distal end thereof;

whereupon, due to the positioning and configuration of the device, the collimated stream released by the delivery nozzle is directed towards a pharyngeal orifice of the eustachian tube, thereafter rapidly reaching and entering into a central lumen of the eustachian tube whereupon the mixture lowers the opening pressure thereof.

11. The method of claim 10 wherein the surfactant constituent of the mixture contained within the canister inserted into the containment section is selected from the group consisting of cholesteryl esters, phospholipids, carbohydrates, and proteins.

12. The method of claim 11 wherein the surfactant constituent is selected to be a phospholipid.

13. The method of claim 12 wherein the propellant constituent of the mixture contained within the canister inserted into the containment section is selected from the group consisting of a fluorocarbon propellant, a chlorofluorocarbon propellant, a hydrofluorocarbons, carbon dioxide or compressed air.

14. The method of claim 13 wherein the phospholipid is selected to be 1,2 dipalmitoyl phosphatidylcholine.

15. The method of claim 14 wherein said method comprises further positioning the device so that, a midline alignment line, formed upon a back surface of the canister containment section, is placed in parallel alignment with a midline of the patient's face.

16. A method for treating otitis media in a human patient utilizing an eustachian tube targeting nasal administration device wherein said device comprises an administration housing having a canister containment section and a delivery nozzle section, said method comprising:

inserting a canister, containing a selected mixture consisting of a selected surfactant constituent and a selected propellent constituent into the canister containment section of the administration device;

positioning the device so that a delivery nozzle, depending from a front surface of the delivery nozzle section, having a central bore demonstrating a longitudinal axis and openings al a proximal and distal end in fluid communication therewith, is placed within and enters a nostril on a selected side of patient's face;

positioning the device so that an elevation alignment arrow, located upon side surfaces of the delivery nozzle section and oriented so as to be in parallel alignment with the longitudinal axis of the central bore of the delivery nozzle, points towards a tragus portion of an ear on the same side of the patient's face as the nostril into which the delivery nozzle is placed and enters;

activating the canister so that a portion of the mixture of surfactant and propellant is released from the canister, flows through conduits formed within the delivery nozzle section and thereafter flows through the central bore of the delivery nozzle wherein, due to a uniform, constant and selected diameter of openings at the proximal end, the distal end and a central bore thereof, the delivery nozzle, forms and releases a collimated stream of the mixture from the distal opening thereof and, due to the size, shape, configuration and positioning of the device, the collimated stream is directed towards the pharyngeal orifice of the eustachian tube, whereupon, the mixture of surfactant and propellant rapidly reaches and enters into a central lumen of the eustachian tube wherein the surfactant lowers the opening pressure of the eustachian tube thereby providing increased patency so as to enable draining of byproducts of otitis media from the middle ear chamber and relief of increased pressure of the middle ear chamber associated therewith.

17. The method of claim 16 wherein the surfactant constituent of the mixture contained within the canister inserted into the containment section is selected from the group consisting of cholesteryl esters, phospholipids, carbohydrates, and proteins.

18. The method of claim 17 wherein the surfactant constituent is selected to be a phospholipid.

19. The method of claim 18 wherein the phospholipid is selected from a class phosphatidlycholine.

20. The method of claim 19 wherein the surfactant constituent is selected to be 1,2 dipalmitoyl phosphatidylcholine.

21. The method of claim 20 wherein the propellant constituent of the mixture contained within the canister inserted into the containment section is selected from the group consisting of a fluorocarbon propellant, a chlorofluorocarbon propellant, a hydrofluorocarbons, carbon dioxide or compressed air.

22. The method of claim 16 wherein the mixture consists of a surfactant constituent, a propellant constituent and a therapeutically active agent effective in the treatment of otitis media.

23. The method of claim 22 wherein the therapeutically active agent effective in the treatment of otitis media is selected from the group consisting of anti-inflammatory, antibiotic, antiviral, decongestant, gene therapy agents.

24. The method of claim 23 wherein the anti-inflammatory agent is selected from the group consisting of betamethasone dipropionate and betamethasone valerate.

25. The method of claim 23 wherein the decongestive agent is selected to be phenylephrine.

26. The method of claim 23 wherein the antibiotic agent is selected from the group consisting of erythromycin, amoxicillin, and a combination of amoxicillin and clavuliic acid.

27. The method of claim 16 wherein the method further comprises positioning the device so that a midline alignment line, located upon the rear portion of canister containment section and oriented so as to be parallel to a longitudinal axis thereof is placed in a parallel alignment with a midline of the face of the patient.

28. The method of claim 16 wherein the method further comprises positioning the device so that an alignment tab, depending from a front surface of the canister containment section, is placed in stable contact with a bridge portion the patient's nose.

29. The method of claim 28 wherein said method further comprises positioning the device so that a second alignment tab, extending from a front surface of the delivery nozzle section, is placed into stable contact with the patient's face just below the nostril in which the administration nozzle enters and is placed.

* * * * *